United States Patent [19]
Shamos

[11] Patent Number: 5,381,487
[45] Date of Patent: * Jan. 10, 1995

[54] PATIENT IDENTIFICATION SYSTEM

[76] Inventor: Morris H. Shamos, 3515 Henry Hudson Pkwy., Bronx, N.Y. 10463

[*] Notice: The portion of the term of this patent subsequent to Dec. 10, 2008 has been disclaimed.

[21] Appl. No.: 761,571

[22] Filed: Sep. 18, 1991

Related U.S. Application Data

[60] Division of Ser. No. 485,828, Feb. 27, 1990, Pat. No. 5,071,168, which is a continuation of Ser. No. 302,023, Jan. 25, 1989, abandoned.

[51] Int. Cl.⁶ .................................................. G06K 9/00
[52] U.S. Cl. ........................................ 382/2; 235/375; 283/69
[58] Field of Search ............... 382/2, 4, 1; 283/68, 283/69, 78, 900

[56] References Cited

U.S. PATENT DOCUMENTS

| | | | |
|---|---|---|---|
| 3,848,112 | 11/1974 | Weichselbaum et al. | 283/900 |
| 4,179,686 | 12/1979 | Bonicalzi et al. | 382/2 |
| 4,476,381 | 10/1984 | Rubin | 283/900 |
| 4,632,428 | 12/1986 | Brown | 283/900 |
| 4,876,725 | 10/1989 | Tomko | 382/2 |
| 4,983,036 | 1/1991 | Froelich | 283/69 |
| 5,054,090 | 10/1991 | Knight et al. | 382/4 |
| 5,071,168 | 12/1991 | Shamos | 382/4 |
| 5,166,498 | 11/1992 | Neele | 235/375 |
| 5,193,855 | 3/1993 | Shamos | 283/117 |
| 5,202,929 | 4/1993 | Lemelson | 382/2 |

FOREIGN PATENT DOCUMENTS

WO8903100 8/1988 Sri Lanka .

OTHER PUBLICATIONS

Renner, S. W., "Phlelsotomists tag Wristband Identification," Cap Today, Jun. 1992.

Primary Examiner—Joseph Mancuso
Assistant Examiner—G. DelRosso
Attorney, Agent, or Firm—Morgan & Finnegan

[57] ABSTRACT

Disclosed is a method of confirming the identity of a patient with an individual to receive a treatment intended for said patient, by (a) obtaining a print indentification characteristic of said patient; (b) obtaining a print identification characteristic of said individual to whom said treatment is intended to be administered; (c) confirming the identity of the print identification characteristic obtained from the patient with the print identification characteristic obtained from the individual. Also disclosed are an associated device and system. The device can have information identifying one or more than one patient.

19 Claims, 2 Drawing Sheets

PATIENT IDENTIFICATION SYSTEM

This is a division of co-pending U.S. application Ser. No. 07/485,828 filed on Feb. 27, 1990, now U.S. Pat. No. 5,071,168 which is in turn a continuation of U.S. application Ser. No. 07/302,023 filed Jan. 25, 1989, now abandoned.

BACKGROUND OF THE INVENTION

1. Field Of The Invention

The present invention relates to the field of patient identification, particularly to methods, devices and systems for confirming the identity of an individual to receive a treatment with the patient for whom the treatment is intended.

2. Brief Description Of The Prior Art

The general use of identification materials for security or law enforcement purposes or credit cards bearing photographs or fingerprints has been the subject of patents and commercially available products. Examples of such patents include, for example, McKee, et al., U.S. Pat. No. 3,709,524; Hollie, U.S. Pat. No. 3,664,910; Nugent, U.S. Pat. No. 3,245,697; English, U.S. Pat. No. 2,712,514; De Gruchy, U.S. Pat. No. 2,395,804; and Voght, U.S. Pat. No. 1,380,506. Commercial security systems including the use of fingerprint identification are available, for example, from Fingermatrix, Inc., North While Plains, N.Y.; Thumbscan, Inc., Oakbrook, Ill.; and Identix, Inc., Palo Alto, Calif.

Drexler, U.S. Pat. No. 4,692,394 discloses a personal identification card on which are recorded visual images, such as a face image or fingerprint, and laser recorded data. By means of in situ laser recording, transaction data, information, or the like related to the photographic image is recorded at subsequent times. For example, insurance claims or medical record entries may be processed sequentially. A photograph of the claimant is alleged to protect against fraudulent use of the card.

Miller, et al., U.S. Pat. No. 3,694,240 discloses an identification system in which an individual's fingerprint is taken at the time identification is to be made and compared to a fingerprint record in a master file of the person the individual purports to be. The prints are taken in the form of transparencies, and those of the master record and those taken at the time of identification are superimposed. The comparison is made by measuring the amount of light passing through the transparencies.

Estrada, U.S. Pat. No. 4,325,570 discloses an identification system which utilizes an individual fingerprint and an identifier which can be correlated to the fingerprint and to a listing of valid identifiers. An identification card is used which has the individual's fingerprint, a grid superimposed over the fingerprint and an identifier printed thereon. The identifier is a series of symbols representing characteristics of the fingerprint. This allows the individual to be identified with a three-point identification check by comparing a new fingerprint of the individual to the fingerprint on the card, comparing the fingerprint on the card to the identifier, and confirming that the identifier is valid by determining if it is included in a list of approved individuals. No suggestion is made of its use in a medical or hospital context.

Systems and methods for positive identification of patients in hospitals and other institutions have been the subject of ongoing efforts at improving reliability.

Relating to hospital or patient care environments, a label printer which makes self-adhesive labels from an identification plate attached to a patient wristband is described in promotional literature from Bio-Logics Products, Inc., Salt Lake City, Utah and in U.S. Pat. No. 4,145,966.

Brown, U.S. Pat. No. 4,632,428 discloses a medical data, identification and health insurance card which carries both visually and machine readable data, including a photograph. It appears primarily to be a compact source of a relatively complete medical history. Brown makes no mention of any use of fingerprints, but does cite other patents relating to medical data cards, including Calavetta, U.S. Pat. No. 3,921,318; Hanna, et al., U.S. Pat. No. 4,031,640; Domo, U.S. Pat. No. 4,236,332; and Anderson, et al., U.S. Pat. No. 4,318,554.

Siegel, U.S. Pat. No. 4,730,849 discloses a device and system for the identification of medication in an attempt to assure that only the patient for whom the medication was prescribed will receive it. A photograph of the patient is affixed to the medication container, in the form of a label, and/or patient record, such as a medication card or chart. Alternatively, upon admission a patient may be issued a "non-removable" identifying wrist band having a machine-readable portion and, optionally, a computer-generated likeness or a miniature photograph of the patient. Before treatment, the coded information on the patient wristband can be compared with that introduced into computerized central records upon admission.

This approach has the disadvantage of relying totally on the integrity of the wrist band, a device which has frequently been known to be removed by patients, or worse, exchanged. There is no direct comparison of the individual appearing for treatment with the admission records of the intended patients.

Notwithstanding the efforts described above, no really reliable method for direct, individually distinctive comparison of a patient, rather than some device or image issued to the patient, with the person appearing for treatment and purporting to be the intended patient has been achieved. Instead, previously available systems have invariably been subject to potential error resulting from human intervention at some point between record entry and treatment.

Disadvantages and risks resulting from misidentification, and resulting erroneous correlation of treatment and individual, include the unnecessary cost and delay to which patients are potentially exposed and, perhaps even more importantly, results in the wasteful utilization of limited treatment facilities.

More critically, in the context of patient treatment, such as surgery, drug or transfusion administration, emergency room trauma or cardiovascular intervention and the like. misidentification of a patient can be life threatening. This is true not only for the patient receiving treatment that was not intended and is inappropriate for the patient but is also potentially life threatening for the patient for whom such critical treatment was intended and who did not receive it because of the misidentification.

SUMMARY OF THE INVENTION

In contrast, the present invention provides the reliability of all machine readable correlation from the arrival of the patient for admission to the appearance of an individual for treatment intended for that patient whose identity can now be incontrovertibly confirmed immediately and at the actual site of treatment. This is achieved without the risks attendant to breaking the chain of computer-confirmation that can result from human interventions by potentially numerous workers who may be unskilled, unfamiliar with the patient in question or both. The invention has resulted from a recognition of, and solution to, this problem and alleviates the risks of medical treatments being administered to individuals other than those for whom the treatment is intended.

A print identification characteristic is a more durable and permanent characteristic than a name, which may be common to several patients, or a photograph, which may bear little resemblance to a individual's appearance after the effects of a disease process or injury. It is particularly unique in its value for treating patients who are unable to communicate, such as those who are unconscious, comatose or are the victims of massive trauma and who may be carrying no identification on them when they appear at the hospital.

Therefore, in one aspect, the present invention provides a method for confirming the identity of an individual to receive a treatment with the patient for whom the treatment is intended. The method includes the steps of (a) obtaining a print identification characteristic of the patient; (b) obtaining a print identification characteristic of the individual to whom the treatment is intended to be administered; (c) confirming the relationship of the print identification characteristic obtained from the patient with the print identification characteristic obtained from the individual. The method can further include preparing a patient identification device such as that described below. The treatment can comprise, for example, obtaining a specimen from or administering a procedure, examination or medication to an individual or delivering newborns from the nursery to the correct mothers. In the latter case, the device would contain a print identification characteristic of both the mother and the newborn, taken upon their respective arrivals. The prints would be compared to scanned prints of individuals believed to be the correct mother and newborn. The print identification characteristic can be, for example, a fingerprint, thumbprint, palmprint, eyeprint, toeprint or heelprint.

In another aspect, the invention provides a patient identification device for confirming the identity of an individual to receive a treatment with the patient for whom the treatment is intended. The device comprises a dimensionally stable base member having affixed thereto visual and machine readable information including at least one print identification characteristic taken from the patient to whom the device was issued and at least one machine-readable representation associated with the print identification characteristic.

In yet another aspect, the invention provides a patient identification system for confirming the identity of an individual to receive a treatment with the patient for whom the treatment is intended. This system comprises (i) a dimensionally stable base member having affixed thereto visual and machine readable information including at least one print identification characteristic taken from the patient to whom the device was issued and at least one machine-readable representation associated with the patient print identification characteristic; (ii) means for comparing the print identification characteristic on the device with at least one print identification characteristic taken from the individual to receive the treatment intended for the patient; and (iii) means for comparing the machine-readable representation on the device with a document or article associated with the treatment to be given. This system can further include means or detectably indicating the identity or non-identity of the patient print identification characteristic with the print identification characteristic of the individual to be treated.

In yet another aspect, the invention provides a system that includes a plurality of treatment stations, each having means for comparing the print identification characteristic on the device described with at least one print identification characteristic taken from the individual to receive the treatment intended for the patient and means for comparing the machine-readable representation on the device with a document or article associated with the treatment to be given; and controller means including means for recording data entered at each treatment station.

DESCRIPTION OF THE PREFERRED EMBODIMENTS

Although specific terms are used in the following description for clarity, they refer only to the particular embodiment(s) selected for illustration and are not a limitation of the scope of the invention.

Figure 1:
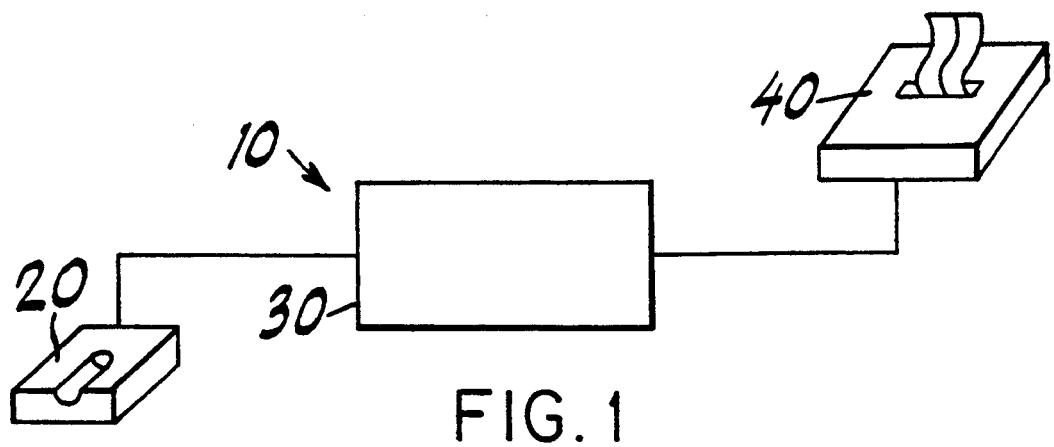
FIG. 1 is a diagrammatic illustration of one embodiment of a print identification characteristic input assembly, particularly suitable for use in small or medium size facilities, and includes a live print scanner, a print data analysis controller and a label printer capable of rendering labels having both visually and machine-readable information printed thereon.

Referring now to FIG. 1, as part of the admission process for each patient, a fingerprint image is taken and stored electronically in the hospital's computer system using print data input assembly 10. Print data assembly 10 includes live print scanner 20, print data analysis controller 30 and, optionally, label printer 40 which produces a label containing the patient's fingerprint in digital format and other data as described in more detail below.

The embodiment illustrated here is particularly suited for a hospital or other institution where all departments are not interconnected by a computer network, such a would be typical of smaller or older facilities, and would require a lesser front-end capital investment to insure patient identity and, therefore, safety. In addition to such smaller hospitals, clinics and facilities used for performing insurance or disability examinations are also appropriate candidates for application of this embodiment.

Label printer 40 is located in the admissions office and, optionally, also in the emergency room or outpatient clinic. Multiple copies of the patient label are made upon patient admission or initial visit and disseminated to those departments where the patient or specimens, such as tissue or body fluid samples, from the patient are to be sent for treatment.

Figure 2:
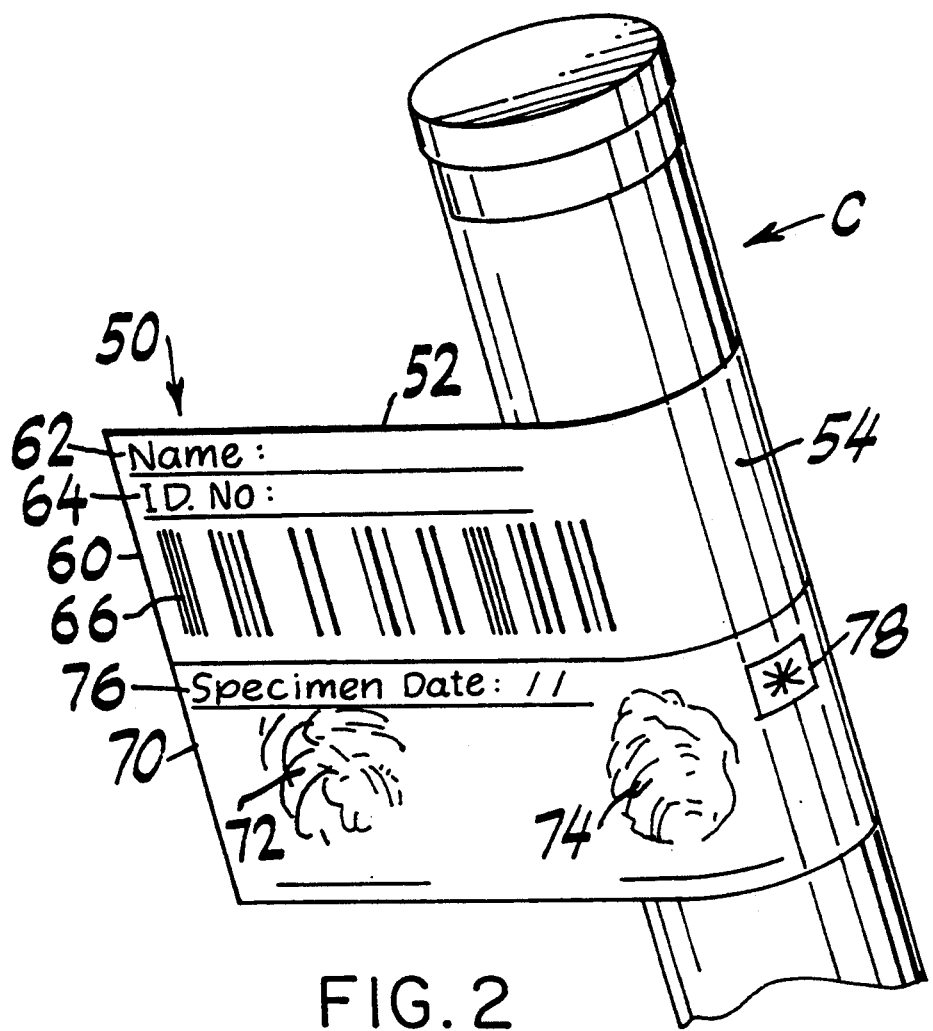
FIG. 2 illustrates a label, such as one produced by the apparatus described with relation to FIG. 1, having patient information thereon, including machine readable information and at least one print identification characteristic thereon and resulting either from the individual receiving a treatment or from the information input obtained at the time of initial patient admission. The label can have information pertaining to one patient or more than one, depending upon its intended use.

Referring now to FIG. 2, specimen or sample container C is provided with patient specimen label 50, which is here shown in more detail. Patient specimen label 50 is formed of a dimensionally stable flexible base 52 which has adhesive on at least a portion of one surface (not shown) and on the other, 14 front surface 54 a machine-readable bar code field 60 and a fingerprint impression field 70.

Machine-readable bar code field 60 is provided with a patient name portion 62, a patient identification number portion 64 and a machine-readable bar code 66 that represents information characterizing the fingerprint(s) taken upon admission, the patient identification number or other data relating to the patient.

In the embodiment selected for illustration, fingerprint impression field 70 is provided with at least one fingerprint area 72 from the fingerprint taken upon admission of the patient and an optional second print area 74. The second print area 74 can be for a print taken from the individual appearing for treatment or from whom the specimen is taken. Fingerprint images can be digital numerical representations of the print's characteristics rather than a literal reproduction of the appearance of the print. Each of print areas 72 and 74 include space, shown here as a line at the bottom of each, for identifying the nature of the print, e.g. right index finger, left thumb, newborn's heel or the like. Fingerprint impression field 70 also includes a date entry portion 76 for identifying the date the specimen and the second fingerprint were taken and a machine-readable print identity confirmation block 78.

The invention further contemplates an embodiment where the label is used to confirm the identity of two separate individuals to confirm correct association of individuals with a relationship. For example, an expectant mother's fingerprint is entered into the hospital record system, upon admission either to the hospital or the delivery room to create a label bearing her print in print area 72. A print impression of the newborn's heelprint is affixed in the delivery room onto second print area 74.

Also, fingerprint impression field 70 can be a blank area reserved for impression of a fingerprint taken from an individual at the time of treatment, particularly where such treatment is simply obtaining a specimen from the individual, which is then compared upon arrival to the laboratory or station where the specimen is to be analyzed. The identity of the individual providing the specimen and the intended patient is confirmed prior to analysis or, at least, prior to reporting of the results of analysis.

Figure 3:
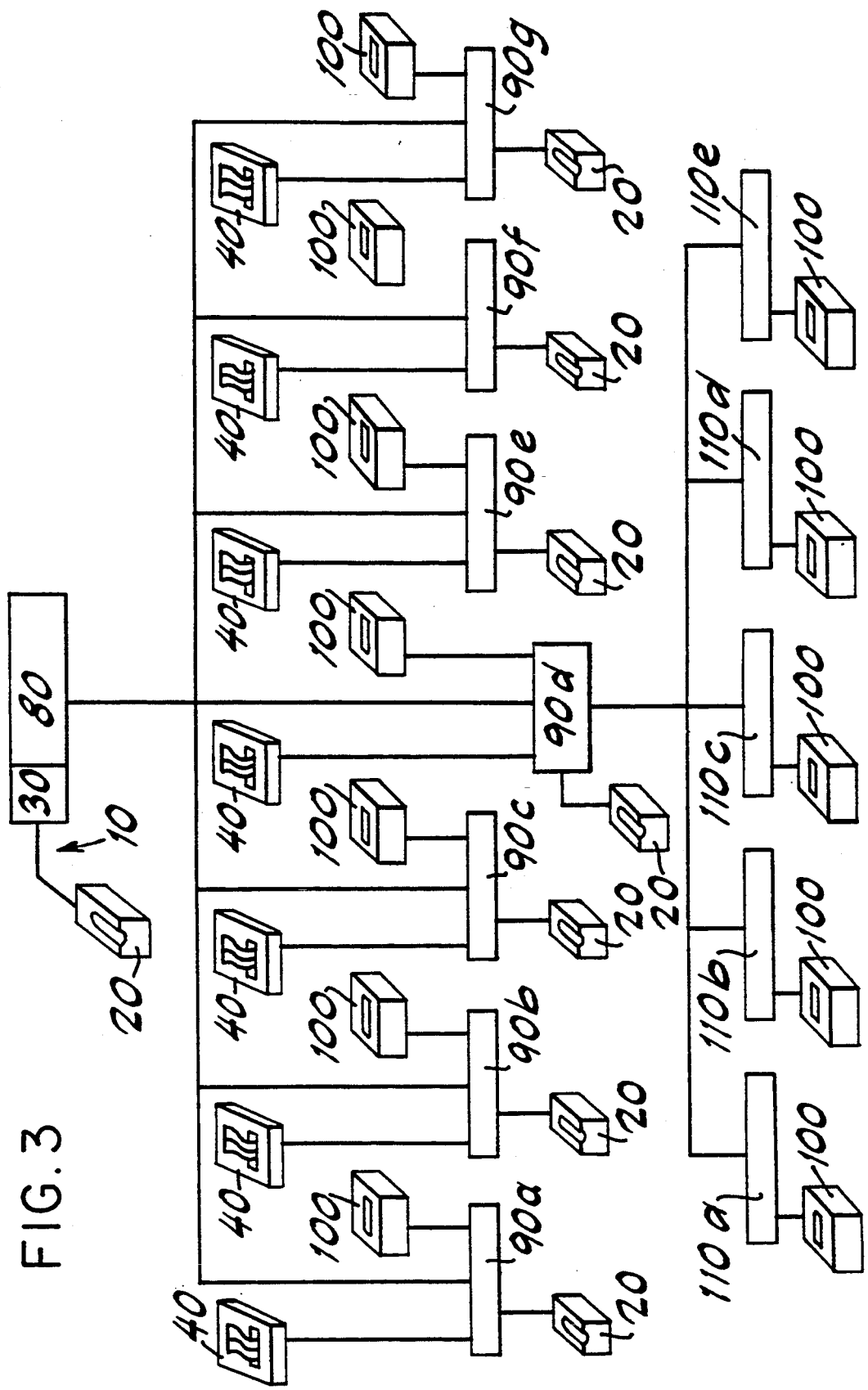
FIG. 3 diagrammatically illustrates a centrally computerized hospital information system in which all hospital departments and stations are able to access information, including print identification characteristic information, obtained upon patient admission and compare it by instrumental analysis with information, particularly print identification characteristics of the individual appearing at that department or station for treatment(s) intended for the patient identified upon admission.

FIG. 3 illustrates a centrally computerized hospital information system in which all departments and stations are able to access a centrally stored computer data bank of patient information. As shown here, print data input assembly 10 includes a live print scanner 20 and a print data analysis controller 30 which is a component of a general purpose digital computer 80 with a stored (fixed) program which is connected to user consoles at each department or station.

General purpose digital computer 80 instructs, monitors, and controls the sequence and coordination of system operations as well as retaining the data bank of patient information made available to the departments and stations of the hospital as and when requested. It can provide data output in any of a variety of formats.

The system illustrated here is particularly suitable for larger or more modern hospitals or institutions. In this embodiment, label printers (not shown) are provided to each department where needed. The individual department generates the labels it needs based upon the information, including fingerprint image and data analysis, obtained from the patient upon admission.

Once admitted to the hospital, a patient may be taken to one or more departments or be visited at the bedside for various treatments. Illustrated examples of such departments or sites to which a patient may be taken for treatment are surgery 90a, obstetrics 90b, radiology 90c, laboratory 90d, bedside drug administration or sample collection 90e, blood bank 90f and dialysis unit 90g. Each of these departments or sites of in-person treatment is provided with a live print scanner 20, label printer 4 and a label reader 100.

Label reader 100 can apply any of a variety of known technologies for scanning machine readable images or information. Examples include those applying laser scanning, digital or analog analysis or holographic analysis.

Other treatments involve samples or specimens obtained from the patient, usually at the bedside, and delivered to laboratory departments where they are analyzed in the absence of the patient. Illustrated examples of such departments are microbiology 110a, cytology 110b, clinical chemistry 110c, hematology 110d and serology 110e.

At least two approaches for confirmation of print identity are contemplated for application at the bedside or elsewhere that portability of an instrument in accordance with the invention along with medical personnel is an important factor. First, the caregiver, such as a phlebotomist, attending the patient can have a portable live print scanner/printer apparatus analogous to that described in FIG. 1 but in an integral portable unit, similar to a laptop computer. Alternatively, prior to taking the sample the caregiver can obtain a print impression from the individual on a tape or paper capable of retaining an image of the print. Either the label printed by the printer or the print exposed tape or paper will have adhesive portions sufficient to permit attachment of the print impression to the specimen container.

The live print so-obtained is then compared to computer memory information, either in a portable computer or upon arrival of a specimen to the laboratory, on the print identification characteristic taken at the time of admission to confirm identity of the individual. This is done at least prior to reporting of the sample analysis results by the remote laboratory and, preferably, using more sophisticated but still readily portable and affordable equipment prior to obtaining the sample. In either case, confirmation is performed prior to reporting the results of analysis and, thus, prior to any treatment predicated thereon.

Although the invention has been described with particularity, numerous changes in the details, combinations and arrangement of elements can be made without departing from the scope of the invention as conceived, described and claimed.

What is claimed is:

1. A patient identification method for confirming the identity of an individual to receive a treatment with the patient for whom said treatment is intended, which method comprises the following sequence of steps:
   a. obtaining a live print identification characteristic of the patient;
   b. storing data representative of said characteristic in an electronic data storage device;
   c. after said data is stored, obtaining at a treatment location a live print identification characteristic directly from said individual to receive a treatment;
   d. comparing said data representative of the print identification characteristic obtained from the patient with data representative of the live print identification characteristic obtained at said treatment location from the individual to receive a treatment; and
   if identity is confirmed by said comparing of data, producing at said treatment location a patient identification device comprising a dimensionally stable base member having affixed thereto identification information of the patient for whom said treatment is intended.

2. The method of claim 1 wherein the print identification characteristic is selected from the group consisting of fingerprint, thumbprint, palmprint, heelprint and toeprint.

3. The method of claim 1 wherein the print identification characteristic is an eyeprint.

4. The method of claim 1 which further comprises the steps of preparing from the patient print identification characteristic patient identification device which comprises a dimensionally stable base member having affixed thereto visual and machine readable information including at least one print identification characteristic taken from the patient whom said treatment is intended and at least one machine-readable representation associated with said patient print identification characteristic.

5. The method of claim 4 wherein said machine-readable representation is a digital representation of said print identification characteristic.

6. The method of claim 3 which further comprises the steps of:
   e. comparing the machine-readable representation on said device with a machine-readable representation on a document or article associated with the treatment to be given to confirm said treatment; and
   f. if identity is confirmed in step d and if said treatment is confirmed in step e by said comparing of machine-readable representations, administering said treatment.

7. The method of claim 6 wherein the comparing in step e patient identification is by an analog analysis.

8. The method of claim 6 wherein the comparing of the print identification characteristics on said patient identification device and of said individual is by laser scanning.

9. The method of claim 6 wherein the comparing of the print identification characteristics on said patient identification device and of said individual is by a digital analysis.

10. The method of claim 6 wherein the comparing of the print identification characteristics on said patient identification device and of said individual is by holographic analysis.

11. The method of claim 1 which further comprises the step of: preserving a paper record of said patient identification device.

12. A patient identification method for confirming the identity of an individual to receive a treatment with the patient for whom said treatment is intended, which method comprises:
   a. obtaining a live print identification characteristic of the patient;
   b. obtaining at a treatment location a live print identification characteristic directly from said individual to receive a treatment,
   c. confirming the identity of the print identification characteristic obtained from the patient with the live print identification characteristic obtained from the individual at said treatment location;
   d. if said identity is confirmed, preparing from the patient print identification characteristic a patient identification device at said treatment location which comprises a dimensionally stable base member having affixed thereto visual and machine readable information including at least one print identification characteristic of the patient and at least one machine-readable representation associated with said patient print identification characteristic;
   e. comparing the machine-readable representation on said device with a machine-readable representation on a document or article associated with the treatment to be given to confirm said treatment; and
   f. if identity is confirmed in step d and if said treatment is confirmed in step e by said comparing of machine-readable representations, administering said treatment.

13. The method of claim 12 which further comprises the step of: preserving a paper record of said patient identification device.

14. The method of claim 12 further comprising the step of obtaining a live print identification characteristic of a second patient, wherein the device is prepared from print identification characteristics from each of said patients.

15. An identification method for confirming the identity of a presenting individual with a known individual, which method comprises the following sequence of steps:
   a. obtaining a live print identification characteristic of the known individual at a first location;
   b. storing data representative of said characteristic in an electronic data storage device;
   c. after said data is stored, obtaining a live print identification characteristic directly from said presenting individual at a second location;
   d. comparing said stored data representative of the print identification characteristic obtained from the known individual with data representative of the print identification characteristic obtained from the presenting individual at said second location; and
   if identity is confirmed between said stored data and the data representative of the print identification characteristic obtained from said presenting individual, producing at said second location a personal identification device comprising a dimensionally stable base member having affixed thereto identification information of said known individual.

16. The method of claim 15 wherein the print identification characteristic is a member of the group consisting of a fingerprint, thumbprint, palmprint, heelprint and toeprint.

17. The method of claim 15 wherein the print identification characteristic is an eyeprint.

18. The method of claim 15 which further comprises the step of preparing said personal identification device which comprises a dimensionally stable base member having affixed thereto visual and machine readable information including at least one print identification characteristic taken from said known individual and at least one machine-readable representation associated with print identification characteristic from said presenting individual.

19. The method of claim 18 wherein said machine-readable representation is a digital representation of said print identification characteristic.

* * * * *

UNITED STATES PATENT AND TRADEMARK OFFICE
CERTIFICATE OF CORRECTION

PATENT NO.    : 5,381,487
DATED         : January 10, 1995
INVENTOR(S)   : Morris H. Shamos It is certified that error appears in the above-identified patent and that said Letters Patent is hereby corrected as shown below:

In claim 4, column 7, line 36, after "characteristic" insert -- said --; line 40, after "patient" insert -- for --.

In claim 7, column 7, line 57, delete "patient identification".

Signed and Sealed this

Twenty-first Day of March, 1995

BRUCE LEHMAN

*Attest:*

*Attesting Officer*      *Commissioner of Patents and Trademarks*